United States Patent [19]
Levine et al.

[11] Patent Number: 5,620,848
[45] Date of Patent: Apr. 15, 1997

[54] METHODS FOR DETECTING MUTANT P53

[75] Inventors: Arnold J. Levine; Thomas E. Shenk, both of Princeton, N.J.; Cathy A. Finlay, Yardley, Pa.

[73] Assignee: Trustees of Princeton University, Princeton, N.J.

[21] Appl. No.: 268,405

[22] Filed: Jun. 30, 1994

Related U.S. Application Data

[63] Continuation of Ser. No. 730,185, Jul. 12, 1991, abandoned, which is a continuation-in-part of Ser. No. 543,963, Jun. 27, 1990, abandoned.

[51] Int. Cl.$^6$ .................................................. C12Q 1/68
[52] U.S. Cl. .............................................. 435/6; 435/7.23
[58] Field of Search ............................... 435/6, 7.1, 7.23, 435/91.1; 436/501, 508, 513, 547, 548, 63, 64, 94, 811, 813; 530/350, 387; 536/23.5

[56] References Cited

U.S. PATENT DOCUMENTS

| | | | |
|---|---|---|---|
| 4,798,787 | 1/1989 | McCormick et al. | 435/7.21 |
| 4,871,838 | 10/1989 | Bos et al. | 536/24.31 |

OTHER PUBLICATIONS

Baker et al., *Science*, vol. 244, 1989, pp. 217–221.
Finlay et al., *Mol. Cell. Biol.*, vol. 8, 1988, pp. 531–539.
Nigro et al., *Nature*, vol. 342, 1989, pp. 705–708.

*Primary Examiner*—James Ketter
*Attorney, Agent, or Firm*—Irving N. Feit; Cheryl L. Becker; Lawrence S. Pope

[57] ABSTRACT

A panel of probes detects and distinguishes between sets of human p53 gene or protein mutations that frequently occur or are selected for in pre-cancer and cancer cells Each set of mutations gives rise to a phenotype that is different from that of wild-type p53 and of at least one other set of p53 mutations.

2 Claims, No Drawings

METHODS FOR DETECTING MUTANT P53

This application is a continuation of Ser. No. 07/730,185, filed Jul. 12, 1991, now abandoned, which is a continuation in part of Ser. No. 07/543,963 filed Jun. 27, 1990, now abandoned, which is incorporated herein by reference.

The present invention is directed to the use of molecular probes in the detection of cancer and pre-cancer states. More particularly, the invention is directed to different cancer and pre-cancer states by means of antibody and DNA probes. The cancer and pre-cancer states are those associated with the p53 protein.

Mutations of proto-oncogenes in somatic cells are increasingly being recognized as significant in the induction of human cancers. Some examples of oncogenes formed by such mutations include: neu, fes, fos, myc, myb, fms, Ha-ras, and Ki-ras. The mutations that convert proto-oncogenes to oncogenes are often point mutations. Much needs to be learned in order to understand how oncogenes and their expression products function to transform normal cells to cancer cells.

Oncogenes are generally believed to act in a dominant fashion. This is generally considered to mean that the conversion of a proto-oncogene to an oncogene results in the acquisition of a new function, i.e., enhancing transformation.

A different type of mutation associated with cancer occurs when a tumor suppressor gene is altered in a way that causes the product of the gene to lose its tumor suppressor function. An example of such a tumor suppressor gene is the retinoblastoma sensitivity gene, Rb. Tumor suppressor genes are sometimes called recessive oncogenes, although, strictly speaking, the products of tumor suppressor genes do not contribute to tumor formation. The phenotype is recessive since, when both alleles are mutated, the absence of a tumor suppressor gene results in an enhancement of tumorigenesis.

The products of certain viral oncogenes are also able to transform cells. Examples of such products include the E6 and E7 proteins from human papilloma virus, the large T antigen from SV40, and E1a from adenovirus. Viral oncogene proteins are believed to bind to and, thereby, to inactivate tumor suppressor proteins, such as the retinoblastoma protein.

A gene product that exhibits some properties of both a dominant and a recessive oncogene is the 53 kd phosphoprotein, p53. Evidence is growing that mutations in the p53 gene is associated with a large number of many types of cancers. For example, Iggo et al., Lancet 335, 675–679 (1990) has expressed the opinion that p53 is the most common proto-oncogene to undergo mutation in lung cancers.

Much of what is known about p53 has been derived from studying the effect of transfecting wild-type and mutant murine p53 in rat embryo fibroblast cells. This work has been reviewed by Levine et al., "The P53 Proto-Oncogene And Its Product," in *Common Mechanisms Of Transformation By Small DNA Tumor Viruses*, L. Villarreal, ed., American Society, for Microbiology, Chapter 2 (1989); Hinds et al., ibid, Chapter 7; and Levine, BioEssays 12, 60–66 (1990).

Briefly, a number of point mutations between amino acids 130 and 240 of p53 (out of 390 amino acids) lead to significant, tumor-promoting changes in phenotype. Both wild-type and mutant p53 are often found at increased levels in transformed cells due to an increase in their metabolic stabilities. The stabilization of mutant p53 is believed to occur through the formation of a complex with cellular proteins, such as the 70 kd heat shock protein, hsc70. The stabilization of wild-type p53 is believed to be associated with its ability to form a complex with the mutant p53-hsc70 complex. These results are consistent with the proposition that alterations in p53 function are involved in the process of cellular transformation. The involvement of mutant murine p53 in the transformation of cells in culture is also apparent from the ability of mutant, but not wild-type, p53 to cooperate with activated Ha-ras to transform primary rat embryo cells.

The p53 gene resides on chromosome 17p. Many cancers, such as those discussed above, are associated with chromosome 17p deletions. Such allelic deletions often indicate the presence of a tumor suppressor gene. The mutation of one allele gives rise to a benign, pre-cancer state. The mutation of the second allele gives rise to the malignant cancer state.

Finlay et al., Cell 57, 1083–1093 (1989), has presented further evidence that wild-type murine p53 displays properties of a suppressor of transformation. Three observations are consistent with this theory.

First, the introduction of wild-type murine p53 into primary rodent cells, along with two cooperating transforming genes, ras and E1 a, results in a decrease in the number of transformed foci. The transformed cell lines that were obtained were found to contain the murine p53 gene, but either failed to express it or produced high levels of an altered murine product. Thus, overexpression of the wild-type murine p53 protein appears to be detrimental to the process of transformation of cultured rat cells by oncogenes.

Second, inactivation of the p53 gene is believed to be associated with the development of Friend virus-induced erythroleukemia in mice (Mowat et al., Nature 314, 633–636 (1985)). There are numerous examples in the literature of tumor cells derived from the spleens of mice infected with the Friend virus complex containing rearrangements or other mutations at the p53 gene locus; see, for example, Ben-David, Oncogene 3, 179–185 (1988).

The third line of evidence consistent with the possibility that the wild-type p53 protein is a member of a group of proteins involved in suppression of transformation is the ability, mentioned above, of p53 to form oligomeric protein complexes with viral oncogenes, such as the SV40 large T antigen, the adenovirus type 5 E1b-55 kd protein, and the human papilloma virus (HPV) type 16 or 18 E6 product; see, for example, Werness, Science 248, 76–79 (1990). Analogous complexes have also been observed between p105, the product of the retinoblastoma susceptibility gene, and the SV40 large T antigen (DeCaprio et al., Cell 54, 275–283 (1988)); the adenovirus E1a protein (Whyte et al., Nature 334, 124–129 (1988)); and the E7 protein of HPV-16 or -18 (Muenger et al., EMBO J. 8, 4099–4105 (1989)).

These interactions between viral proteins and p 105 are thought to inactivate a growth-suppressive function of p105, thus mimicking deletions and mutations commonly found in the retinoblastoma gene in tumor cells. Similarly, oligomeric protein complex formation between these same viral proteins and p53 may eliminate or alter the growth-suppressive function of p53; see Finlay et al., id.

The clonal nature of p53-related tumors is consistent with a tumor progression model in which non-neoplastic pre-cancer cells bearing a wild-type p53 gene and a mutated p53 gene have a distinct proliferative advantage over normal cells, which contain two wild-type genes. The advantage is due to mutant p53-mediated interference with wild-type p53 function. The increased proliferative capacity of such non-neoplastic cells increases the probability of a second, inactivating mutation, i.e., gene conversion or deletion, at the p53 locus. The resulting cells, which now contain mutations in both p53 alleles, are able to express the fully neoplastic phenotype; see Finlay et al., id., and Baker et al., Science 244, 217–221 (1989).

The above model is supported by the discovery that human tumor cells from which a 17p chromosome allele been deleted contain mutations in the remaining allele. The mutations tended to be clustered in four "hot spots," which coincided with the four most highly conserved regions of the p53 gene; see Nigro et al., Nature 342, 705–708 (1989).

Gannon et al., EMBO J. 9, 1595–1602 (1990), propose that all human mutant p53 proteins are recognized by a monoclonal antibody, PAb240. These authors suggest that all p53 mutants exert a common conformational effect, which results in expression of the PAb240 epitope.

OBSERVATIONS OF THE INVENTORS THAT FORM THE BASIS OF THE PRESENT INVENTION

Previously unpublished experiments of the inventors relating to human p53 form the basis of the present invention. Different human p53 clones isolated from colorectal carcinomas possess mutations at amino acid residues 143, 175, 273 or 281 (out of a total of 393 residues). Such p53 mutants, when co-transfected into rat embryo fibroblasts (REFs) with activated wild-type ras oncogenes, cooperate with the oncogenes to transform the REFs in culture. All of the transformed cell lines derived from these experiments produce the human p53 protein in elevated levels.

The mutations are summarized in Table 1. The effect of the mutations on properties of human p53 mutant proteins is shown in Table 2.

TABLE 1

Mutations of Human p53 Protein

| Clone | DNA | | Protein | |
|---|---|---|---|---|
| | Nucleotide | Alteration | Residue | Alteration |
| p53-c143A | 430 | T -> C | 143 | val -> ala |
| p53-175H | 526 | G -> A | 175 | arg -> his |
| p53-273H | 820 | G -> A | 273 | arg -> his |
| p53-281G | 844 | A -> G | 281 | asp -> gly |

TABLE 2

Properties of Human p53 Mutant Proteins

| Clone | Relative Tx Frequency | Half-life Protein | hsc Bound | p90 Bound | Tumors in Nude Mice |
|---|---|---|---|---|---|
| p53-cWT[1] | 0 | 20 min. | − | + | + |
| p53-c143A[1] | 1.6 | 1.5–2 hrs. | + | + | + |
| p53-WT[2] | 0 | ND[3] | ND[3] | ND[3] | ND[3] |
| p53-175H[2] | 11.5 | 3.6–6.4 hrs. | + | + | + |
| p53-273H[2] | 4.7 | 7 hrs. | − | + | + |
| p53-281G[2] | 1.9 | 3.5 hrs.[4] | − | + | ND[3] |

[1]- cDNA. Does not contain introns.
[2]- contains introns.
[3]- Not Determined
[4]- half-life estimated in cell lines expressing ras + E1a + mutant p53

In order to obtain the results shown in Table 2, cDNA clones or partial cDNA-genomic clones of p53, plus the activated ras oncogene, were co-transfected into primary rat embryo fibroblasts. In each set of transfections, transformed foci were scored two to three weeks later in duplicate cell cultures;.

The results in Table 2 demonstrate that mutant human p53, cDNA or cDNA-genomic hybrid clones derived from colon carcinomas can behave as dominant oncogenes and cooperate with the ras oncogene in transforming rat embryo fibroblasts. Four different missense mutations, at amino acids residues 143, 175, 273 and 281, each contributed to the transformed phenotype. In all these cases, the human p53 mutant protein was produced in high levels in the transformed cell at least in part due to the extended half-life of these mutant proteins.

Unexpectedly, the phenotypes of cells containing the different mutants are not the same. For example, in one experiment, the three p53 DNA clones containing "hot spot" mutations at codons 175, 273, and 281, i.e., p53-175H, p53-273H, and p53-281G, had characteristic and reproducible transformation frequencies (number of foci produced) in a ratio of 6:2.4:1, indicating that these "hot spot" mutations are not equivalent in their phenotypes. In another experiment, the 175 mutant allele was 3–10 times more efficient than the 273 mutant allele in cooperating with the ras oncogene in transforming primary rat cells in culture.

More striking is the fact that p53-175H and p53-c143A mutant proteins bind to hsc70 in transformed cells while the p53-273H and p53-281G mutant proteins do not detectably interact with or bind to hsc70. Previous experiments have shown that some mutant murine p53 proteins have an altered conformation (Hinds et al., Mol. Cell. Biol.7, 2363–2869 (1987); Finlay et al., Ibid. 8., 531–539 (1988)). It is possible that such altered p53 molecules bind to hsc70 and sequester wild-type p53 in a complex that blocks proper folding, assembly or localization of p53. Thus, p53-c143A and p53-175H may represent mutant proteins which never fold correctly and thus retain their affinity for hsc70. If wild-type p53 is recruited into this complex, the p53-mutant-hsc70-p53-wild-type complex would poison the function of wild-type p53.

This cannot be the case for the p53-273H and p53-281G mutants, which, as mentioned above, do not bind to hsc70. The p53-273H human mutant protein can associate with the rat p53 protein and form an oligomeric complex as demonstrated by co-immunoprecipitation with a human-specific antibody, Ab-2. This complex is not mediated by hsc70 and may be less efficient in sequestering the rat cellular wild-type p53 protein. This is consistent with a poorer ability to transform cells in culture.

In contrast to co-transfections with activated ras plus mutant human p53, co-transfections with activated ras plus wild-type human p53 resulted in a very low frequency of focus formation, and only one focus could be cloned into an established cell line. Thus, it appears likely that mutation of human p53 activates a dominant transforming function that is not detectable in wild-type p53.

In summary, it now appears that all of the human p53 mutant proteins differ from the wild-type human p53 protein by having an extended half-life, by being expressed at higher levels, and by possessing the ability to transform cells in culture. These data support the suggestion that mutation of p53 on one allele could have a growth-promoting phenotype in vivo, which expands the number of cells with such mutations and favors the selection of a second mutational event (deletion or gene conversion) in the cancer cells. The observation that many tumor cells retain only the mutant p53 allele suggests that these mutant proteins are not fully dominant over the wild-type allele, or that the mutants continue to confer a proliferative advantage on cells in the absence of wild-type p53. Such a positive effect of mutant p53 on cell proliferation in the absence of wild-type p53 could be an intrinsic function of the molecule, or could be mediated by titration of cellular proteins other than endogenous p53, for example, via the protein p90.

Most significantly, the results establish that there are classes of human p53 mutations that give rise to pre-cancer and cancer cells with different phenotypes. It is apparent that these different phenotypes can give rise to cancers that take different courses and have different prognoses.

A problem with present methods to detect cancer is that these different phenotypic changes have not been taken into account. This problem is addressed by the present invention.

A second problem addressed by the present invention is to determine how the different phenotypic changes affect the course and prognosis of cancer. Once this problem has been solved, a further problem is to be able to detect the various phenotypic changes in order to be able to predict the course a cancer will take and the best way to treat such cancer.

SUMMARY OF THE INVENTION

These and other problems as will be apparent to those having ordinary skill in the art have been solved by providing a panel of probes that detect and distinguish between sets of human p53 gene or protein mutations that frequently occur or are selected for in pre-cancer and cancer cells, each set giving rise to a phenotype that is different from that of wild-type p53 and of at least one other set of p53 mutants.

The invention further relates to a method of distinguishing between sets of human p53 gene or protein mutations that are frequently occurring or selected for in pre-cancer or cancer cells, each set giving rise to a phenotype that is different from the wild-type gene or protein and from at least one other set of mutations, the method comprising determining the mutations in a sample of p53 genes or proteins with a panel of probes that detect and distinguish between such sets.

The invention also provides a method of distinguishing between sets of human p53 DNA or protein mutations that are frequently occurring or selected for in pre-cancer or cancer cells. The method comprises the steps of determining whether such a mutation exists and, if so, whether the mutant: protein binds to the heat shock protein, hsc70, less tightly than mutant human p53 protein known to bind strongly to hsc70, such as p53-143A (valine at codon or amino acid position 143 of native p53 mutated to alanine) or p53-175H (arginine at codon or amino acid position 143 of native p53 mutated to histidine).

DETAILED DESCRIPTION OF THE INVENTION

Definitions

The present invention is directed to the detection of mutations in wild-type p53 genes and proteins. For the purposes of the present specification, the term "wild-type" p53 means the nucleotide or amino acid sequence reported by Matlashewski et al., EMBO J. 13, 3257–3262 (1984); Zakut-Houri et al., EMBO J. 4, 1251–1255 (1985); and Lamb and Crawford, Mol. Cell. Biol. 5, 1379–1385 (1986). The sequences are available from GenBank. Wild-type p53 includes a proline/arginine polymorphism at amino acid 72 and the corresponding nucleotide polymorphism.

The detection of mutations in wild-type p53 genes and proteins is important, since such mutations indicate pre-cancer and cancer states. There are no apparent limitations in regard to the type of cancer that is associated with a p53 mutation. Such cancers include, generally, colorectal, lung, ovarian, cervical, adrenal cortex, bone, bladder, breast, brain, and mesenchyme cancers and, more specifically, chronic myelocytic leukemia, chronic myelogenous leukemia, and osteogenic sarcomas.

A pre-cancer cell is defined as a cell that has one normal p53 allele and one mutated p53 allele. The mutation is usually a point mutation.

In a cancer cell, both alleles are mutated. One mutation is usually a point mutation, as described above for a pre-cancer cell. The other mutation is usually a deletion of all or a significant part of the p53 gene.

Mutations

The invention is based on the unexpected discovery that there are sets of mutations in p53 that correspond to sets of different conformations and different phenotypes. It is important to determine as many sets of mutations as possible. It is not, however, necessary to determine each individual mutation within a set. A set of mutations is defined as having at least one mutation and giving rise to a phenotype that is different from the wild type and at least one other set of mutations.

Each set of phenotypes leads to a distinguishable course and severity of the same disease. Therefore, by determining sets of mutations, a physician can not only determine that a patient has a particular cancer, but can distinguish different subsets of prognoses and prescribe the best treatment.

For example, many colorectal cancers give rise to mutations at or near amino acid positions 143, 175, 273 and 281 of p53. These mutations are described in Table 1.

Families suffering with the Li-Fraumeni syndrome contain p53 mutations that cluster between codons 245 and 258. A mutation at codon 248 is particularly prevalent. These families have a high incidence of cancer.

Mutations in the same region of p53 implicated in the Li-Fraumeni syndrome are also frequently found in hepatocellular carcinomas. A mutation at codon 249 is frequently found in patients with liver cancer.

It should be emphasized that any single nucleotide or amino acid that is mutated or any region of the p53 gene or protein within which one or more mutation occurs constitutes a set of mutations in accordance with the present invention as long as the set of mutations satisfies the definition given above. In one embodiment of the invention, for example, sets of mutations comprise residues 117–142, 171–181, 234–258, and 270–288 of the p53 protein as well as the corresponding nucleotides of the p53 gene.

In another embodiment of the invention, one set of mutations comprises mutations at amino acids 143 and 175. A second set of mutations comprises mutations at amino acids 273 and 281.

Panel of Probes

In general, a panel of probes in accordance with the invention includes at least two members. There may, for example, be as many as three, four, five or six sets of mutations and, therefore, the same number of probes. There may be as many as 8, 10, or 12 probes, and, in fact, even more.

The mutations in a set are commonly found in various types of human tumors. The ubiquitous nature of these mutations may result from their frequent occurrence or, as explained above, because they provide a proliferative advantage to cells containing them and, therefore, are selected for.

Alterations in either the nucleotide sequence of the gene or the amino acid sequence of the protein may be assayed in order to determine whether a mutation within one of the sets of mutations in accordance with the present invention exists. Alterations in the amino acid sequence may be probed by antibodies. Alterations in the nucleotide sequence may be probed by means of nucleotide probes or, in some cases, by restriction endonucleases. Nucleotides as used herein refer to RNA or DNA.

Antibody Probes

An "antibody" in accordance with the present specification is defined broadly as a polypeptide that binds specifically to an epitope. The antibody may be polyclonal or monoclonal. Antibodies further include recombinant polyclonal or monoclonal Fab fragments prepared in accordance with the method of Huse et al., Science 246, 1275–1281 (1989).

Methods for preparing polyclonal and monoclonal antibodies that exhibit specificity toward single amino acid differences between oncogenes are described by McCormick et al. in U.S. Pat. No. 4,798,787. These methods are incorporated herein by reference.

Briefly, polyclonal antibodies may be produced by injecting a host mammal, such as a rabbit, mouse, rat, or goat, with the p53 protein or a fragment thereof capable of producing antibodies that distinguish between mutant p53 and wild-type p53. The peptide or peptide fragment injected may contain the wild-type sequence or the mutant sequence. Sera from the mammal are extracted and screened to obtain polyclonal antibodies that are specific to the peptide or peptide fragment.

In order to produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein in Nature 256, 495–497 (1975). In order to be useful, a peptide fragment must contain sufficient amino acid residues to define the epitope of the p53 molecule being detected.

If the fragment is too short to be immunogenic, it may be conjugated to a carrier molecule. Some suitable carrier molecules include keyhold limpet hemocyanin and bovine serum albumen. Conjugation may be carried out by methods known in the art. One such method is to combine a cysteine residue of the fragment with a cysteine residue on the carrier molecule.

The peptide fragments may be synthesized by methods known in the art. Some suitable methods are described by Stuart and Young in "Solid Phase Peptide Synthesis," Second Edition, Pierce Chemical Company (1984).

A variety of assays are available for detecting proteins with labelled antibodies. Such methods may involve one step or two steps. In a one-step assay, the target p53 molecule, if it is present, is immobilized and incubated with a labelled antibody. The labelled antibody binds to the immobilized p53. After washing to remove unbound molecules, the sample is assayed for the presence of the label.

In a two-step assay, immobilized p53 is incubated with an unlabelled antibody. The p53-unlabelled antibody complex, if present, is then bound to a second, labelled antibody that is specific for the unlabelled antibody. The sample is washed and assayed for the presence of the label, as described above.

The label may be a radioactive atom, an enzyme, or a chromophoric moiety. Some examples of radioactive atoms include $P^{32}$, $I^{25}$, $H^3$, and $C^{14}$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avadin or -streptavadin, and antibody-antigen.

Oligonucleotide Probes

The probes of the present invention may also be oligonucleotides that distinguish wild-type from mutant DNA or RNA. The oligonucleotide probes may be prepared by methods known in the art. Suitable methods for synthesizing oligonucleotide probes are described by Caruthers in Science 230, 281–285 (1985).

The oligonucleotide probes may contain a sequence complementary to a sequence of wild-type or mutant p53 that comprises a nucleotide involved in a mutation. For example, the nucleotide involved in a mutation may be that at position 430, 526, 820, or 844 of wild-type or mutant p53.

The length of the oligonucleotide probe is not critical, as long as it is capable of hybridizing to a test sample containing wild-type or mutant p53 and distinguishing between the two. The oligonucleotide should contain at least 6 nucleotides, preferably at least 10 nucleotides, and, more preferably, at least 15 nucleotides.

The oligonucleotide probes are labelled for detection. The labels that can be conjugated to oligonucleotide probes for detection are the same as those that are conjugated to antibodies. Such labels are described above. Conjugating the labels to the oligonucleotides is achieved by methods known in the art.

There is no upper limit to the length of the oligonucleotide probes. Longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Methods for distinguishing wild-type oncogenes from mutants containing a single nucleotide change are described in PCT Application WO 87/07646. These methods are incorporated herein by reference.

Briefly, oligonucleotides containing either the wild-type or mutant sequence are hybridized under stringent conditions to dried agarose gels containing target p53 RNA or DNA digested with an appropriate restriction endonuclease. Suitable stringent conditions include two degrees below the calculated $T_m$ of a perfect duplex. The oligonucleotide probe hybridizes to the target p53 detectably better when the probe and the target p53 are perfectly complementary.

The target p53 DNA is optionally amplified in order to improve the sensitivity of the assay. Amplification may be accomplished by methods known in the art. A suitable method is the polymerase chain reaction method, as described in Mullis et al., U.S. Pat. Nos. 4,683,195 and 4,683,202.

A particularly convenient method for assaying a single point mutation by means of oligonucleotides is described in Segev, PCT Application WO 90/01069, licensed to ImClone Systems Incorporated, New York City. This method is limited to cases wherein the nucleotide in wild type p53 that is mutated and the corresponding nucleotide in the mutant are not complementary.

Briefly, two oligonucleotide probes for each wild-type or mutated p53 strand being assayed are prepared. Each oligonucleotide probe is complementary to a sequence that straddles the nucleotide that either becomes or has been mutated. Thus, a gap is created between the two hybridized probes.

For example, in order to distinguish between wild type and mutant forms of p53, wherein the guanine at position 526 in the wild type form is mutated to adenine, probes that leave a gap at position 526 are prepared. The gap is filled with a mixture of a polymerase, a ligase, and the nucleotide complementary to that at position 526 to form a ligated oligonucleotide product. For example, if wild-type p53 is being detected, the gap is filled with cytosine. The mutant form will not be detected under these conditions.

On the other hand, if the mutant form is being detected, the gap will be filled with thymine. The wild-type p53 will not be detected under these conditions. Either of the oligonucleotides or the nucleotide filling the gap may be labelled by methods known in the art.

The ligated oligonucleotide product can be amplified by denaturing it from the p53, hybridizing it to additional oligonucleotide complement pairs, and filling the gap again, this time with the complement of the nucleotide that filled the gap in the first step.

To illustrate the method, structure (1) shows a pair of oligonucleotide probes hybridizing to wild-type p53 containing guanine at position 526. Structure (2) shows the gap between the two probes being filled with cytosine. Structure (3) shows the ligated oligonucleotide product from structure (2) hybridizing to two additional complementary oligonucleotides. Structure (4) shows the gap in Structure (3) being filled with guanine. This process can be repeated as often as is desired.

STRUCTURES

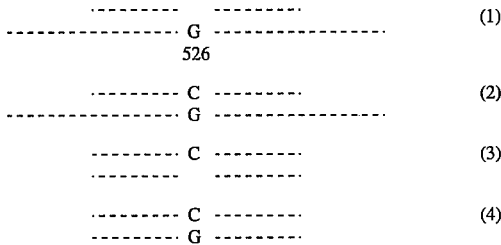

Following ligation of a ligated oligonucleotide product and, optionally, amplification, the oligonucleotide product is separated by size and the label is detected by methods known in the art. The description of the above procedure from PCT Application WO 90/01069 is incorporated herein by reference.

RESTRICTION ENDONUCLEASE PROBES

Mutations may also be detected if they create or abolish restriction sites. For example, the Hha I site is GCGC. The mutation in the human p53 gene at nucleotide 430 from thymine to cytosine creates an Hha I site. Such a mutation alters the amino acid sequence at residue 143 from valine to alanine; see Table 1.

A mutation of the human p53 gene at nucleotide 526 from guanine to adenine abolishes an Hha I site. Such a mutation causes an alteration at residue 175 from arginine to histidine; see Table 1.

Accordingly, the mutations indicated in Table 1 at residues 430 and 526 of the human p53 gene may be detected by restriction analysis; see Baker et al., Science 244, 217–221 (1989). Some additional examples of the use of restriction analysis to assay point mutations is given in Weinberg et al., U.S. Pat. No. 4,786,718.

Some additional methods for distinguishing polynucleotide sequences differing by one nucleotide are described by De Ley et al., J. Bacteriol. 101, 738–754 (1970); Wood et al., Proc. Natl. Acad. USA 82, 1585–1588 (1985); Myers et al., Nature 313, 495–497 (1985); and Myers et al., Science 230, 1242–1246 (1985). These methods are incorporated herein by reference.

ASSAYS

The labeled probes described above are capable of distinguishing wild-type and sets of mutant forms of p53. Confirmation may be obtained by comparing the response of the probes to the different forms. The wild-type p53 gene and protein are known, and may be obtained by known methods, such as those described in Matlashewski et al., EMBO J. 13, 3257–3262 (1984); Zakut-Houri et al., EMBO J. 4, 1251–1255 (1985); and Lamb and Crawford, Mol. Cell. Biol. 5, 1379–1385 (1986). Mutants may be prepared from wild-type p53 by site-directed mutagenesis; see, for example, Zoller and Smith, Nucl. Acids Res. 10, 6487–6500 (1982); Methods in Enzymology 100, 468–500 (1983); and DNA 3, 479–488 (1984).

Wild-type and mutant p53 structural genes may also be synthesized by known methods, such as by preparing overlapping double-stranded oligonucleotides, filling in the gaps, and ligating the ends together. The DNA may be cloned in a suitable host cell and expressed. The p53 DNA and protein may be recovered from the host cell. See, generally, Sambrook et al., "Molecular Cloning," Second Edition, Cold Spring Harbor Laboratory Press (1987).

Assays involving antibody and DNA probes are conducted in accordance with methods known in the art. The assay may be designed so that the probes test positive for wild-type p53 and negative for mutant p53. In such a case, it is preferable to use an oligonucleotide probe, which will not be affected by the specific mutation.

On the other hand, the probes may test positive for mutant p53 and negative for wild-type p53. In such a case, it is preferable to use antibodies, which detect protein. The preference for antibody probes is due to the presence of higher concentrations of mutant p53 protein than wild-type p53 protein in transformed cells.

It has unexpectedly been found that at least one set of human p53 mutants does not detectably bind to the heat shock protein hsc70 or, at least, binds significantly less tightly than mutant human p53 protein known to bind strongly to hsc70, such as p53-143A (valine at codon or amino acid position 143 of native p53 mutated to alanine) or p53-175H (arginine at codon or amino acid position 175 of native p53 mutated to histidine). See Tables 1 and 2 above. The set of human p53 mutants that does not detectably bind, or binds less tightly, to hsc70 comprises mutations at amino acid positions 273 (arginine at codon or amino acid position 273 of native p53 mutated to histidine) and 281 (aspartic acid at codon or amino acid position 281 of native p53 mutated to glycine). Therefore, sets of p53 mutations may be distinguished from other sets of mutants by determining first whether any mutation exists and, if so, how tightly the mutants bind to hsc70.

Methods for determining relative binding affinities may be conducted by methods known in the art. For example, a method for determining whether a p53 protein binds to hsc70 is described by Finlay et al. in Mol. and Cell. Biol. 8, 531–539 (1988) and by Hinds et al. in Mol. and Cell. Biol., 7, 2863–2869 (1987). The method described in these papers, which is incorporated herein by reference, involves co-immunoprecipitation experiments with anti-p53 and anti-hsc70 antibodies.

A suitable antibody specific for hsc70, for example, may be prepared from the sera of rabbits immunized with the carboxy-terminal 21 amino acids of a 70 kd heat shock protein family member, hsp70, as described in the Hinds et al. article, Id. The method of preparing the antibody as described in the Hinds et al. article is incorporated herein by reference.

When the wild type or mutated p53 gene is transfected into rat embryo fibroblast (REF) cells, the REF cells express the p53 protein; see above. p53 may be isolated and purified by known methods. For example, the cells may be lysed and the p53 protein immunoprecipitated by adding p53-specific antibodies to solutions or suspensions of the protein. The immunoprecipitates are recovered by centrifugation. See Hinds et al., Cell Growth and Differentiation 1, 571–580 (1990); Finlay et al., Cell 57, 1083–1093 (1989) and Hinds et al., Molecular and Cell Biology 7, 2863–2869 (1987).

The co-immunoprecipitation may also be performed by means of an antibody affinity column using conditions suitable for purifying p53 with a PAb421 immunoaffinity column. See Clarke et al. in Molecular and Cellular Biology 8, 1206–1215 (1998).

It has surprisingly been found that, when subjected to the above procedures, the p53 protein co-immunoprecipitates with a protein that has a molecular weight of 90 kD, called p90. Suitable antibodies for the co-immunoprecipitation include PAb421 and Ab2. PAb421 recognizes the carboxy-terminus of p53 from various species, including human, mouse and rat p53, and is described by Harlow et al. in the Journal of Virology 39, 861–869 (1981). Ab2 is specific for the amino-terminus of human p53, and is available from Oncogene Science, Inc. of Manhassett, N.Y. The p90 protein does not immunoprecipitate when REF cells that do not express p53 are treated in the same way with the same antibodies.

Following centrifugation or elution from the column, p90 may be separated from the p53/p90 complex by means of SDS PAGE. The single band at 90 kD is cut and sequenced. A partial sequence of p90 obtained from transformed rat embryo fibroblast cells is:

VAQMLLSQESDDYSQPST (see SEQ.ID.NO:1)

Another method for purifying p90 is that generally described by Aebersold et al., Proc. Natl. Acad. Sci. USA 84, 6970–6974 (1987).

Mammals other than rats have proteins that are homologous to rat p90. A protein is homologous to p90 if it co-immunoprecipitates with p53 under the conditions described above and has substantially the same sequence as p90—i.e., is at least about 30% identical, preferably at least about 50% identical, and more preferably at least about 75% identical to the rat p90 protein.

The p90 protein or its homolog may also be prepared by well known recombinant DNA methods, such as those described by Sambrook, Fritsch and Maniatis (eds) in *Molecular Cloning, A Laboratory Manual*, Second Edition, Cold Spring Harbor Laboratory Press (1989). Briefly, this method involves providing DNA that encodes the protein; amplifying or cloning the DNA in a suitable host; expressing the DNA in a suitable host; and harvesting the protein.

PROVIDING DNA

DNA encoding p90 is isolated by using the partial amino acid sequence provided above or a fragment thereof to prepare one or more oligonucleotide probes. The probe is labelled and used to screen a genomic or cDNA mammalian library in a suitable vector, such as in phage lambda. The homology between the DNA of the D53 from the species being screened and that of rat p53 is taken into account in determining the conditions for the hybridization.

The DNA isolated is sequenced, and the sequence used to prepare additional oligonucleotide probes. This procedure may be repeated to obtain overlapping fragments until a complete open reading frame is produced.

SCREENING GENOMIC DNA WITH OLIGONUCLEOTIDE PROBES

Methods for determining whether an oligonucleotide probe recognizes a specific nucleic acid molecule in a sample are known in the art. Preferably, the target nucleic acid molecule is immobilized. The presence of probe hybridized to the target nucleic acid molecule indicates the presence of the nucleic acid molecule in the sample. Examples of some suitable screening methods are described by Dallas et al. in "The Characterization of an *Escherichia Coli* Plasmid Determinant that Encodes for the Production of a Heat-labile Enterotoxin." in K. N. Timmis and A. Puehler; eds, *Plasmids of Medical, Environmental, and Commercial Importance,* Elsevier/North-Holland Publishing Co., Amsterdam, pages 113–122 (1975); Grunstein and Hogness in Proc. Natl. Acad. Sci USA 72, 3961–3965 (1975); Palva et al. in U.S. Pat. No. 4,731,325, which is assigned to Orion-yhtyma, Espoo, Finland; Mullis et al. in U.S. Pat. No. 4,683,195, which is assigned to Cetus Corporation, Emeryville, Calif.; Schneider et al. in U.S. Pat. No. 4,882, 269, which is assigned to Princeton University, and Segev in PCT Application WO 90/01069. The Schneider et al. patent and the Segev application are both licensed to ImClone Systems Inc., New York City.

AMPLIFYING DNA

The DNA obtained may be amplified by methods known in the art. One suitable method is the polymerase chain reaction (PCR) method described by Saiki et al. in Science 239, 487 (1988), by Mullis et al. in U.S. Pat. No. 4,683,195 and by Sambrook, Fritsch and Maniatis (eds) in *Molecular Cloning, A Laboratory Manual,* Second Edition, Cold Spring Harbor Laboratory Press (1989). It is convenient to amplify the clones in lambda-gt10 or lambda-gt11 vectors using lambda-gt10 or lambda-gt11-specific oligomers as the Amplimers (available from Clontech, Palo Alto, Calif.).

Restriction fragments are cloned into a suitable vector, such as a plasmid or bacteriophage, and sequenced in accordance with methods known in the art. A suitable sequencing method is the dideoxy chain terminating method described by Sanger et al. in Proc. Natl. Acad. Sci. USA 74, 5463–5467 (1977).

Suitable vectors and polymerases for sequencing are known. A suitable vector is the Bluescript vector of Stratagene. A suitable polymerase is Sequenase (United States Biochemical Corp., Cleveland, Ohio).

EXPRESSING DNA

The DNA encoding the protein of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

The vector into which the vector is spliced may comprise segments of chromosomal, non-chromosomal and synthetic DNA sequences. Some suitable prokaryotic cloning vectors include plasmids from *E. coli*, such as colE1, pCR1, pBR322, pMB9, pUC, pKSM, and RP4. Prokaryotic vectors also include derivatives of phage DNA such as fd, M13, and other filamentous single-stranded DNA phages.

Vectors for expressing proteins in bacteria, especially *E. coli*, are also known. Such vectors include the pKK233 plasmid family (or any of the tac family of plasmids), T7, and lambda $P_L$. Examples of vectors that express fusion proteins include the PATH vectors described by Dieckmann and Tzagoloff in J. Biol. Chem. 260, 1513–1520 (1985). The PATH vectors contain DNA sequences that encode anthranilate synthetase (TrpE) followed by a polylinker at the carboxy terminus. Other expression vector systems are based on beta-galactosidase (pEX); maltose binding protein (pMAL); glutathione S-transferase (pGST)—see Gene 67, 31 (1988) and Peptide Research 3, 167 (1990). Vectors useful in yeast are available. A suitable example is the 2u plasmid.

Suitable vectors for use in mammalian cells are also known. Such vectors include well-known derivatives of SV-40, adenovirus, retrovirus-derived DNA sequences and vectors derived from combination of plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al., "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. Natl. Acad. Sci. USA 77, 4216–4220, (1980).

Useful expression hosts include well-known prokaryotic and eukaryotic cells. Some suitable prokaryotic hosts include, for example, *E. coli*, such as *E. coli* SG936, *E. coli* HB 101, *E. coli* W3110, *E. coli* X1776, *E. coli* X2282, *E. coli* DHI, and *E. coli* MRCI, Pseudomonas, Bacillus, such as *Bacillus subtilis*, and Streptomyces. Suitable eukaryotic cells include yeasts and other fungi, insect, animal cells, such as COS cells and CHO cells, human cells and plant cells in tissue culture.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

FUSION PROTEINS

The proteins may be purified by methods known in the art. For example, the entire protein or portions thereof may be expressed in the form of a fusion protein with an appropriate fusion partner. The fusion partner preferably facilitates purification and identification. Some useful fusion partners include beta-galactosidase (Gray, et al., Proc. Natl. Acad. Sci. USA 79, 6598 (1982)); trpE (Itakura et al., Science 198, 1056 (1977)); protein A (Uhlen et al., Gene 23 369 (1983)); glutathione S-transferase (Johnson, Nature 338, 585 (1989)); Van Etten et al., Cell 58, 669 (1989)); and maltose binding protein (Guan et al., Gene 67, 21–30 (1987); Maina et al., Gene 74, 36–373 (1988); Riggs, P., in Ausebel, F. M. et al. (eds) Current Protocols in Molecular Biology, Greene Associates/Wiley Interscience, New York (1990)).

Such fusion proteins may be purified by affinity chromatography using reagents that bind to the fusion partner. The reagent may be a specific ligand of the fusion partner or an antibody, preferably a monoclonal antibody. For example, fusion proteins containing beta-galactosidase may be purified by affinity chromatography using an anti-beta-galactosidase antibody column (Ullman, Gene. 29, 27–31 (1984)). Similarly, fusion proteins containing maltose binding protein may be purified by affinity chromatography using a column containing cross-linked amylose; see Guan, European Patent Application 286,239.

Optionally, the DNA that encodes the fusion protein is engineered so that the fusion protein contains a cleavable site between the protein and the fusion partner. Both chemical and enzymatic cleavable sites are known in the art. Suitable examples of sites that are cleavable enzymatically include sites that are specifically recognized and cleaved by collagenase (Keil et al., FEBS Letters 56, 292–296 (1975)); enterokinase (Hopp et al., Biotechnology 6, 1204–1210 (1988)); factor Xa (Nagai et al., Methods Enzymol. 153, 461–481 (1987)); and thrombin (Eaton et al., Biochemistry 25, 505 (1986)). Collagenase cleaves between proline and X in the sequence Pro-X-Gly-Pro wherein X is a neutral amino acid. Enterkinase cleaves after lysine in the sequence Asp-Asp-Asp-Asp-Lys. Factor Xa cleaves after arginine in the sequence Ile-Glu-Gly-Arg. Thrombin cleaves between arginine and glycine in the sequence Arg-Gly-Ser-Pro.

Specific chemical cleavage agents are also known. For example, cyanogen bromide cleaves at methionine residues in proteins.

PURIFYING PROTEINS

The recombinant protein is purified by methods known in the art. Such methods include affinity chromatography using specific antibodies. Alternatively, the recombinant protein may be purified using a combination of ion-exchange, size-exclusion, and hydrophobic interaction chromatography using methods known in the art. These and other suitable methods are described by Marston, "The Purification of Eukaryotic Proteins Expressed in *E. coli*" in *DNA Cloning*, D. M. Glover, Ed., Volume III, IRL Press Ltd., England, 1987.

p90 may be used to prepare antibodies that are capable of co-immunoprecipitating p53. p53 may be isolated from the precipitate and purified. The anti-p90 antibodies may be polyclonal or monoclonal.

Polyclonal and monoclonal antibodies may be prepared by methods known in the art. See above and Campbell, "Monoclonal Antibody Technology, The Production and Characterization of Rodent and Human Hybridomas" in Burdon et al., Eds, Laboratory Techniques in Biochemistry and Molecular Biology, Volume 13, Elsevier Science Publishers, Amsterdam (1985).

SEQUENCE LISTING

What we claim is:

1. A method of assessing a mutation in a human p53 gene from a patient comprising comparing 1) the degree of binding of the protein, encoded by said gene, to heat shock protein hsc70, with 2) the degree of binding of another mutant human p53 protein known to bind strongly to heat shock protein hsc70, wherein said resulting comparison indicates the type of cancer and severity of cancer in said patient possessing said mutation.

2. The method of claim 1 wherein said mutant human p53 protein is selected from the group consisting of p53-143A or p53-175H.

* * * * *

UNITED STATES PATENT AND TRADEMARK OFFICE
CERTIFICATE OF CORRECTION

PATENT NO. : 5,620,848
DATED : April 15, 1997
INVENTOR(S) : Arnold J. Levine, et. al.

It is certified that error appears in the above-identified patent and that said Letters Patent is hereby corrected as shown below:

Column 2, line 6, insert the following:

--The U.S. government has a paid-up license in this invention and the right in limited circumstances to require the patent owner to license others on reasonable terms as provided for by the terms of grant no. 5 P01 CA 41086 awarded by the National Institute of Health.--

Signed and Sealed this

Sixteenth Day of November, 1999

*Attest:*

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Val Ala Gln Met Leu Leu Ser Gln Glu Ser Asp Asp Tyr Ser Gln Pro
1               5                   10                  15
Ser Thr